US012669466B2

(12) United States Patent
Baesler

(10) Patent No.: US 12,669,466 B2
(45) Date of Patent: Jun. 30, 2026

(54) ELECTROCHEMICAL SENSOR ARRANGEMENT, BREATHALYZER AND METHOD FOR DETERMINING A VITALITY OF ELECTRODES OF AN ELECTROCHEMICAL SENSOR

(71) Applicant: Dräger Safety AG & Co. KGaA, Lübeck (DE)

(72) Inventor: Malte Baesler, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 682 days.

(21) Appl. No.: 18/008,708

(22) PCT Filed: May 27, 2021

(86) PCT No.: PCT/EP2021/064198
§ 371 (c)(1),
(2) Date: Dec. 7, 2022

(87) PCT Pub. No.: WO2021/254760
PCT Pub. Date: Dec. 23, 2021

(65) Prior Publication Data
US 2023/0221279 A1 Jul. 13, 2023

(30) Foreign Application Priority Data

Jun. 16, 2020 (DE) .......................... 102020115804.1

(51) Int. Cl.
*G01N 27/416* (2006.01)
*A61B 5/00* (2006.01)
(Continued)

(52) U.S. Cl.
CPC ......... *G01N 27/4163* (2013.01); *A61B 5/082* (2013.01); *A61B 5/4845* (2013.01); *G01N 27/3275* (2013.01)

(58) Field of Classification Search
CPC .............. G01N 21/3504; G01N 21/88; G01N 21/8845; G01N 21/2045;
(Continued)

(56) References Cited

U.S. PATENT DOCUMENTS 5,202,637 A * 4/1993 Jones ................... G01N 33/007
324/425
5,273,640 A * 12/1993 Kusanagi ........... G01N 27/4175
204/415
(Continued)

FOREIGN PATENT DOCUMENTS

CN 102854303 A 1/2013
CN 103874922 A 6/2014
(Continued)

OTHER PUBLICATIONS

Becquerel, Alexandre Edmond, Mémoire sur les effets électriques produits sous l'influence des rayons solaires. Comptes rendus hebdomadaires des séances de l'Academie des sciences, 1839, 9. Jg., S. 561-567.
(Continued)

*Primary Examiner* — Tran M. Tran
(74) *Attorney, Agent, or Firm* — McGlew and Tuttle, P.C.

(57) ABSTRACT

An electrochemical sensor arrangement (10) for a breath alcohol measuring device (100), to a corresponding breath alcohol measuring device (100) as well as to a process for determining a vitality of electrodes of an electrochemical sensor. The electrochemical sensor arrangement comprises an electrochemical sensor with at least two electrodes (12, 14). The electrochemical sensor arrangement further comprises a heat source (16). The heat source is arranged such that it, upon activation, selectively heats one of the electrodes (12) of the electrochemical sensor.

22 Claims, 3 Drawing Sheets

(51) Int. Cl.
_A61B 5/08_ (2006.01)
_G01N 27/327_ (2006.01)

(58) Field of Classification Search
CPC ....... G01N 2035/00415; G01N 33/007; G01N
33/0006; G01N 33/4972; G01N 25/72;
G01N 25/4826; G01N 25/482; G01N
2015/035; G01N 2223/632; G01M
11/0292; G01M 11/0278
See application file for complete search history.

(56) References Cited

U.S. PATENT DOCUMENTS

| | | | | |
|---|---|---|---|---|
| 5,733,436 | A | * | 3/1998 | Demisch ............ G01N 27/4163 |
| | | | | 205/785.5 |
| 5,759,368 | A | | 6/1998 | Kuhn |
| 6,404,205 | B1 | * | 6/2002 | Kitamura ............. G01N 33/004 |
| | | | | 204/431 |
| 6,428,684 | B1 | * | 8/2002 | Warburton ......... G01N 27/4163 |
| | | | | 204/406 |
| 6,629,444 | B2 | * | 10/2003 | Peng .................. G01N 27/4163 |
| | | | | 73/1.06 |
| 7,017,386 | B2 | * | 3/2006 | Liu .................... G01N 27/4163 |
| | | | | 73/1.06 |
| 7,090,755 | B2 | * | 8/2006 | Inoue ................ G01N 27/4175 |
| | | | | 73/1.06 |
| 7,959,777 | B2 | * | 6/2011 | Scheffler ........... G01N 33/0006 |
| | | | | 204/406 |
| 8,005,629 | B2 | * | 8/2011 | Steinmueller ...... G01N 27/4165 |
| | | | | 702/34 |
| 8,377,275 | B2 | * | 2/2013 | Ieda .................... G01N 33/007 |
| | | | | 204/426 |
| 8,543,340 | B2 | * | 9/2013 | Tice .................. G01N 33/0006 |
| | | | | 708/200 |
| 8,888,987 | B2 | * | 11/2014 | Schattke .............. G01N 33/007 |
| | | | | 204/430 |
| 9,057,690 | B2 | * | 6/2015 | Smith .................. G01N 27/404 |
| 9,128,045 | B2 | * | 9/2015 | Mayer ............... G01N 27/4163 |
| 9,209,468 | B2 | * | 12/2015 | Chen ................. H01M 8/04552 |
| 9,291,484 | B2 | * | 3/2016 | Rakow ................... G01F 25/00 |
| 9,316,614 | B2 | * | 4/2016 | Stock ..................... A61B 5/082 |
| 9,851,342 | B2 | * | 12/2017 | Kaneko ............... G01N 33/445 |
| 10,132,784 | B2 | * | 11/2018 | Mealy, Jr. ........... G01N 33/007 |
| 10,132,786 | B2 | * | 11/2018 | Diekmann ......... G01N 33/0073 |
| 10,234,417 | B2 | * | 3/2019 | Davis ................ G01N 27/4073 |
| 10,309,944 | B2 | * | 6/2019 | Hopka .................... F01N 11/00 |
| 10,823,718 | B2 | * | 11/2020 | Murata .................. G05D 23/19 |
| 11,112,378 | B2 | * | 9/2021 | Scheffler ............. G01N 27/413 |
| 11,209,385 | B2 | * | 12/2021 | Diekmann ......... G01N 27/4163 |
| 11,408,851 | B2 | * | 8/2022 | Ross .................. G01N 27/4045 |
| 11,680,933 | B2 | * | 6/2023 | Brown .............. G01N 33/0006 |
| | | | | 73/23.2 |
| 11,860,175 | B2 | * | 1/2024 | Scheffler .......... G01N 35/00693 |
| 12,188,915 | B2 | * | 1/2025 | Brown ................. G01N 27/404 |
| 12,216,078 | B2 | * | 2/2025 | Haupt ..................... A61B 5/082 |
| 12,235,235 | B2 | * | 2/2025 | Wohltjen ........... G01N 27/4141 |
| 2003/0037590 | A1 | * | 2/2003 | Stark ................... G01N 33/007 |
| | | | | 73/1.06 |

| | | | | |
|---|---|---|---|---|
| 2004/0040842 | A1 | * | 3/2004 | King ..................... G01N 27/42 |
| | | | | 204/434 |
| 2006/0078467 | A1 | | 4/2006 | Stock |
| 2008/0110241 | A1 | * | 5/2008 | Rothschild .......... G01N 27/125 |
| | | | | 73/31.06 |
| 2013/0226470 | A1 | * | 8/2013 | Kaneko ............... G01N 23/083 |
| | | | | 702/34 |
| 2017/0184537 | A1 | * | 6/2017 | Umasankar ........ G01N 27/4065 |
| 2019/0036136 | A1 | * | 1/2019 | Wolf, Jr. ........... G01N 33/4972 |
| 2020/0278332 | A1 | * | 9/2020 | Schlichte .......... G01N 33/0006 |
| 2021/0288194 | A1 | * | 9/2021 | Wang ...................... H02S 10/00 |
| 2022/0178895 | A1 | * | 6/2022 | Tschuncky ......... G01N 33/0006 |
| 2022/0268722 | A1 | * | 8/2022 | Osswald ............... G01N 25/30 |
| 2023/0236168 | A1 | * | 7/2023 | Granstam ........... G01N 33/007 |
| | | | | 73/23.3 |

FOREIGN PATENT DOCUMENTS

| | | |
|---|---|---|
| CN | 110208326 A | 9/2019 |
| DE | 19619169 A1 | 11/1997 |
| DE | 102012017638 B3 | 8/2013 |
| DE | 102019003021 A1 | 10/2020 |
| DE | 102019003994 A1 | 12/2020 |
| JP | 2018530757 A | 10/2018 |
| KR | 101947047 B1 | 2/2019 |
| WO | 9918430 A1 | 4/1999 |
| WO | 2014143175 A1 | 9/2014 |

OTHER PUBLICATIONS

Trawka, Maciej, et al. Fluctuation Enhanced Gas Sensing with WO3-based nanoparticle Gas Sensors Modulated by UV Light at Selected Wavelengths. Sensors and Actuators B:Chemical, 2016, 234. Jg., S. 453-461.

Rahman, Mohammad R., et al. The Application of Power-Generating Fuel Cell Electrode Materials and Monitoring Methods to Breath Alcohol Sensors. Sensors and Actuators B: Chemical, 2016, 228. Jg., S. 448-457.

Ozoemena, Kenneth I., et al. Fuel Cell-Based Breath-Alcohol Sensors: Innovation-Hungry Old Electrochemistry. Current Opinion in Electrochemistry, 2018, 10. Jg., S. 82-87. Electrochemistry, 2018, 10. Jg., S. 82-87. https://www.researchgate.net/profile/Adewale_Ipadeola/publication/325196489_Fuel_cell-based_breath-alcohol_sensors_Innovation-hungry_old_electrochemistry/links/5c39b024458515a4c71ff816/Fuel-cell-based-breath-alcohol-sensors-Innovation-hungry-old-electrochemistry.pdf.

Modjtahedi, Ali; et al.. Low Catalyst Loaded Ethanol Gas fuel Cell Sensor. Sensors and Actuators B: Chemical, 2016, 234. Jg., S. 70-79.

Ghavidel, Mohammadreza Zamanzad et al., Fuel Cell-Based Breath Alcohol Sensors Utilizing Pt-Alloy Electro-catalysts. Sensors and Actuators B: Chemical, 2018, 273. Jg., S. 574-584.

Dräger Alcotest® 6820 Atemalkohol-Vortest- Gerät Firmenschrift 2015. URL: https://www.draeger.com/Products/Content/alcotest-6820-pi-9041690-de-de.pdf [rech. 21-01-2021].

Allan, Jesse TS et al. The Influence of Relative Humidity on the Performance of Fuel Cell Catalyst Layers in Ethanol Sensors. Sensors and Actuators B: Chemical, 2017, 239. Jg., S. 120-130.

* cited by examiner

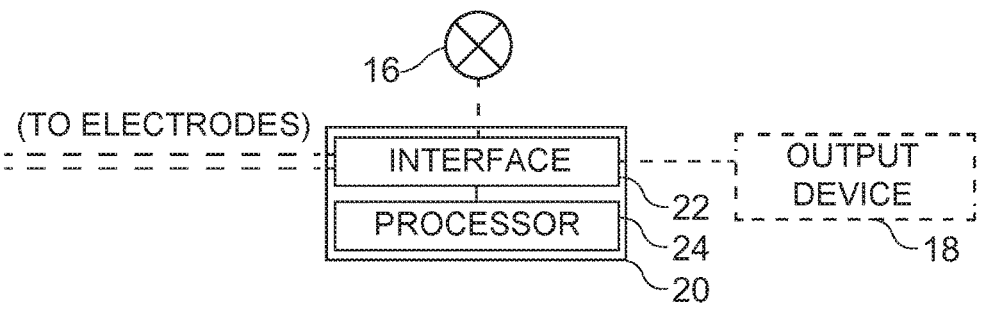
Fig. 2b
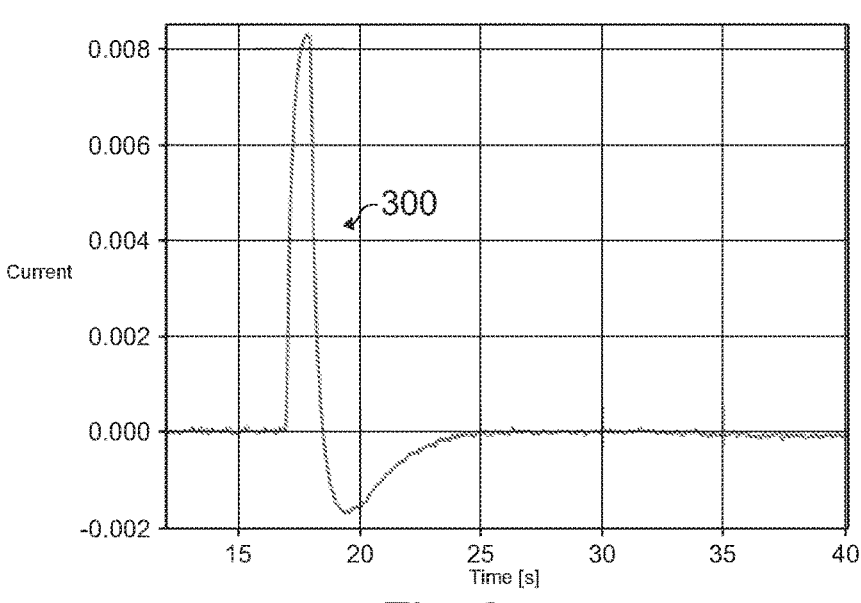
Fig. 3a
Fig. 3b

ELECTROCHEMICAL SENSOR ARRANGEMENT, BREATHALYZER AND METHOD FOR DETERMINING A VITALITY OF ELECTRODES OF AN ELECTROCHEMICAL SENSOR

CROSS REFERENCE TO RELATED APPLICATIONS

This application is a United States National Phase Application of International Application PCT/EP2021/064198, filed May 27, 2021, and claims the benefit of priority under 35 U.S.C. § 119 of German Application 10 2020 115 804.1, filed Jun. 16, 2020, the entire contents of which are incorporated herein by reference.

TECHNICAL FIELD

The present invention pertains to an electrochemical sensor arrangement for a breath alcohol measuring device, to a corresponding breath alcohol measuring device (breathalyzer) as well as to a process for determining a vitality of electrodes of an electrochemical sensor, for example, for measuring the vitality of an electrochemical sensor.

BACKGROUND

Breath alcohol measuring devices measure the concentration of alcohol in the breath of humans. Electrochemical sensors, whose action principle is the fuel cell, are used for mobile measuring devices, but also partially for evidential use. The sensitivity of the electrochemical sensor may vary due to a change in the ambient conditions, especially due to aging and change in humidity or change in concentration of the aqueous electrolytes. Some chemical operations of the sensor generally slow down due to drying out, and this [sensor] becomes slower. The sensor may be accelerated again by remoistening. The drying out (desiccation) and remoistening processes are in this case not entirely reversible, so that the sensor may degenerate over time. Also, the sensor temperature has an effect on the sensor dynamics. In some alcohol sensors, for example, the sensor velocity doubles when the sensor becomes hotter by about 12° C. In this case, the vitality of the electrodes is dependent on a degeneration of the electrochemical sensor because of drying out.

Slow, degenerated sensors are usually detected during the adjustment, for example, via an analysis of the sensor velocity by means of gassing with the target gas. In this case, for example, the rate of analysis is determined and this is, in some cases, temperature-compensated.

The drawback of the above-mentioned approaches is that the vitality can only be detected at the time of the adjustment. In the time in-between, i.e., during operation in the field, a slow sensor cannot be detected. However, an early warning of weak sensors is desirable from the customer's point of view.

SUMMARY

There is a need for an improved concept for determining a vitality of an electrochemical sensor, which makes it possible to determine the vitality during operation in the field.

This need is taken into account by the electrochemical sensor arrangement as well as by the process of the independent claims.

The present invention is based on the finding that the determination of the vitality of the electrodes of an electrochemical sensor can be carried out by one of the electrodes of the electrochemical sensor being heated selectively, by a voltage being formed between the electrodes, and a flow of current, which is formed due to the reduction of this voltage, can be analyzed to determine the vitality of the electrodes of the electrochemical sensor. Such a selective heating of one of the electrodes is carried out by a heat source, which is provided as part of the electrochemical sensor arrangement. The generation of the corresponding voltage is thus also possible in the field independently of an adjustment apparatus. This property may be utilized to carry out the corresponding vitality determination at short intervals by the customer himself. The determination of the vitality can thus be triggered at regular intervals or be triggered manually by the customer. This results in the reliable detection of vitality in the field without a gassing test in at least some exemplary embodiments. The customer may, as a result, be warned early to replace the sensor (in the sense of a predictive maintenance). Compensation parameters can further be adapted during the operation on the basis of the vitality. As a result, the accuracy of the devices can be improved. The adjusting intervals can be extended due to the adaptation of the parameters, or a readjustment may even be dispensed with in case of some devices.

Exemplary embodiments of the present invention create an electrochemical sensor arrangement for a breath alcohol measuring device. In this case, the electrochemical sensor arrangement is not limited to breath alcohol measurements. On the contrary, the electrochemical sensor arrangement may also be used in other contexts. For example, the electrochemical sensor arrangement may be an electrochemical sensor arrangement for a gas measuring device. The electrochemical sensor arrangement comprises an electrochemical sensor with at least two electrodes. The electrochemical sensor arrangement further comprises a heat source. The heat source is arranged such that it, upon activation, selectively heats one of the electrodes of the electrochemical sensor. A voltage is generated between the two electrodes due to the selective heating of the one electrode. If the electrodes are connected via a measuring resistor, then a current flows, which is then analyzed in order to determine the vitality of the particular electrochemical sensor, for example, during operation in the field.

In at least some exemplary embodiments, the heat source is a light source, for example, a light-emitting diode (LED). Consequently, a contactless heating of the one electrode is possible, as a result of which the present invention may also be used with existing electrochemical sensors without structural changes of the actual sensor. Another advantage of the LED is that this has a high efficiency and primarily emits light. This [light] penetrates a plastic housing of the sensor only with minimal attenuation and is first adsorbed on the dark electrodes. Consequently, one of the electrodes is selectively heated. In addition, the heating is carried out in a contactless manner. As a result, the introduction of energy can be switched off and switched on again very rapidly and the sensor responds with very steep current measured curves.

For example, a voltage can be generated between the electrodes due to the selective heating of the one electrode. This voltage can, in turn, result in a flow of current which can be analyzed in order to determine the vitality of the electrochemical sensor.

In various exemplary embodiments, the electrochemical sensor arrangement further comprises a control device. The control device is configured to determine the vitality of the electrodes based on the selective heating of the one electrode, for example, based on the voltage generated, and based on the flow of current generated thereby. For example, the control device may be configured to carry out the process proposed below. As a result, the electrochemical sensor arrangement or the breath alcohol measuring device with the electrochemical sensor arrangement can be put into a position to determine the vitality of the electrodes in the field.

In some exemplary embodiments, the electrochemical sensor arrangement further comprises a graphic output unit to output information on a vitality of the sensor. In this connection, the information on the vitality of the electrodes is determined based on the selective heating of the one electrode. For example, the control device can be configured to output the information on the vitality of the sensor via the graphic output unit. As a result, the information on the vitality may be provided to a user of the electrochemical sensor arrangement, for example, of the breath alcohol measuring device. The user is enabled, based on this information, to decide when an adjustment or a replacement of the sensor is to be carried out, or whether the electrochemical sensor is still sufficiently accurate.

Exemplary embodiments of the present invention further create a breath alcohol measuring device comprising the electrochemical sensor arrangement. As a result, the breath alcohol measuring device can be put into a position to test the vitality of the integrated electrochemical sensor.

Exemplary embodiments of the present invention further create a process for determining a vitality of electrodes of an electrochemical sensor. The process comprises an activation of a heat source over a predefined time period in order to selectively heat one of the electrodes of the sensor. The process further comprises the determination of the flow of current between the electrodes of the electrochemical sensor. The flow of current is based on a voltage, which is caused by the one selective heating of the one electrode by the heat source. As a result, there is a current measuring resistance between the electrodes. The process further comprises a determination of the vitality of the sensor based on a signal shape of the flow of current. Such a process can be carried out by components, which can be integrated in the device which comprises the electrochemical sensor, as a result of which a test of the electrochemical sensor in the field is made possible.

In some exemplary embodiments, the process further comprises a provision of information on the vitality of the sensor via a graphic output unit. A user of the electrochemical sensor can, based on this information, be enabled to decide when an adjustment or a replacement of the sensor is to be carried out, or whether the electrochemical sensor is still sufficiently accurate.

For example, the information on the vitality of the sensor may comprise information on an estimated remaining duration of a usability of the electrochemical sensor, taking a predefined minimal measuring accuracy into consideration. This enables the user to estimate how long he will still be able to operate the corresponding sensor in the device.

The process is carried out by a device, which comprises the electrochemical sensor and the heat source, in various exemplary embodiments. In this case, the process may be carried out as part of a self-test of the device. This makes possible a routine testing of the electrochemical sensor, without needing a separate testing device for this.

The process further comprises a determination of a compensation parameter based on the vitality of the sensor in some exemplary embodiments. The compensation parameter depicts to what extent the vitality of the sensor has an effect on the measurements of the sensor. The process may further comprise a carrying out of measurements by means of the electrochemical sensor, taking the compensation parameter into consideration. For example, it is possible for a given vitality of the sensor to know to what extent the measured values differ from the actual values. This knowledge can be used to determine the compensation parameter based on the determined vitality of the electrochemical sensor.

Some examples of the devices and/or processes are explained in more detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2b is a schematic block diagram of an exemplary embodiment of a control device for determining a vitality of electrodes of an electrochemical sensor;

FIG. 3a is a graph showing measured values of an electrochemical sensor in an exemplary test setup;

FIG. 3b is a graph showing measured values of a healthy and of a dried-out (desiccated) electrochemical sensor in another exemplary test setup;

DESCRIPTION OF PREFERRED EMBODIMENTS

Figure 1:
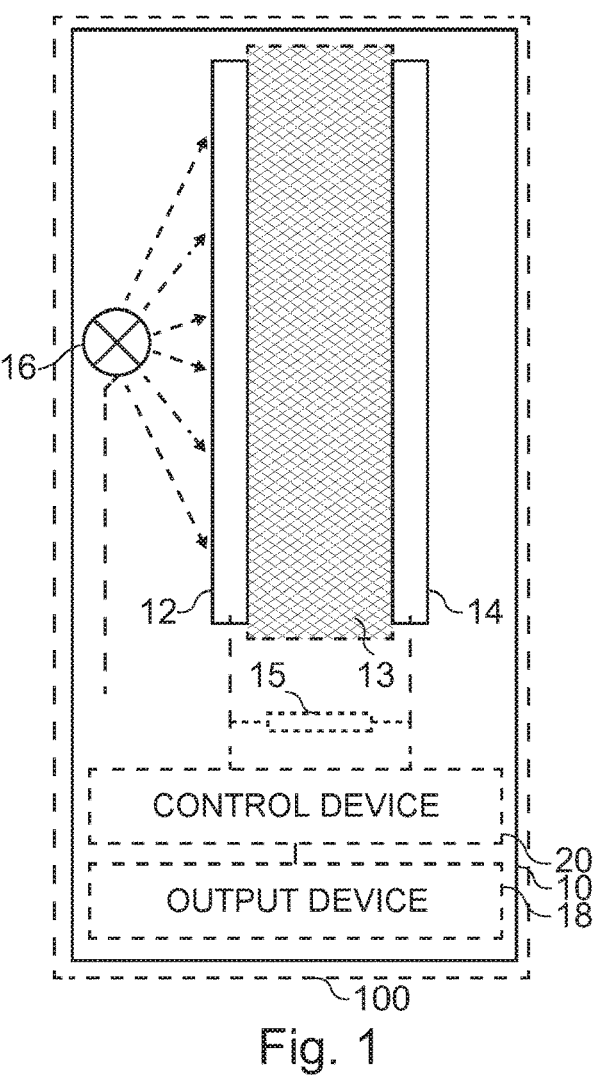
FIG. 1 is a schematic diagram of an exemplary embodiment of an electrochemical sensor arrangement as well as of a breath alcohol measuring device with such an electrochemical sensor arrangement.

Referring to the drawings, different examples are now described in more detail with reference to the attached figures. In the figures, the boldness of lines, layers and/or areas is exaggerated for illustration.

Other examples may cover modifications, correspondences and alternatives, which fall within the scope of the disclosure. Identical or similar reference numbers pertain in the entire description of the figures to identical or similar elements, which may be embodied identically or in a modified form in a comparison with one another, while they provide the same or a similar function.

It is obvious that, when an element is described as being "connected to" or "coupled with" another element, the elements can be connected or coupled directly or via one or more intermediate elements. When two elements A and B are combined using an "or," it is to be understood that all possible combinations are disclosed, i.e., only A, only B as well as A and B, if not explicitly or implicitly defined otherwise. An alternative wording for the same combinations is "at least one of A and B" or "A and/or B." The same applies, mutatis mutandis, to combinations of more than two elements.

The present disclosure deals with an electrochemical sensor arrangement, for example, for a breath alcohol measuring device, as well as with a process for determining the sensor vitality of electrochemical sensors in the field, especially of alcohol sensors, via a thermal excitation, for example, by means of light (e.g., from an LED). The test can be carried out at any time and does not need the use of a test gas.

The electrochemical sensor works as a fuel cell. Under the effect of, for example, ethyl alcohol, this [ethyl alcohol] is electrochemically burned with the oxygen in the air and electric energy is released in the process. In an exemplary embodiment, the current is measured by means of a 4.3-Ohm shunt resistor and a precise 24-bit delta-sigma converter. Currents are measured in the nano-ampere range in the process, i.e., a low-noise electronic measuring device is needed.

If the electrochemical sensor is thermally balanced, then no voltage is present at its electrodes and thus no current is flowing. The measured value is 0. However, if the one electrode of the sensor is heated more intensely than the other electrode, i.e., a temperature gradient is present in the sensor, then a thermoelectric voltage, which is expressed in a flow of current, is generated. The zero point of the sensor in the device is shifted as a result. This process is generally undesirable, so that the sensor must be thermally balanced for accurate measurement, so that its zero point does not drift.

If two identical electrodes in an electrolyte are irradiated with UV light with different intensity, it is then possible to measure a voltage between the two electrodes. This effect was discovered in 1839 by Alexandre Edmond Becquerel and is named after him as the Becquerel effect. The electrochemical sensor and the alcohol sensor in particular is, however, nothing more than such a cell. If the electrochemical sensor is irradiated with UV light, then a voltage is generated on the electrodes. The reason is that, due to the irradiation, electrons can be raised to a higher energy level due to photon adsorption. These [electrons] lead to an increase in potential in case of an electrochemical sensor.

Both effects, i.e., the flow of current resulting from a thermoelectric voltage as well as resulting from a photoelectric voltage, can be utilized in this invention. On the one hand, a thermoelectric voltage is generated by the brief, one-sided heating of the sensor and, on the other hand, a photoelectric voltage is generated due to irradiation by means of UV light. Both brief voltage generations lead to a current curve, which can be analyzed correspondingly.

If a sensor was thermally or photoelectrically brought out of balance, then a fast sensor is capable of compensating for the disturbance rapidly. A slow sensor needs more time for this. In addition, the dynamics of a weak sensor looks different.

FIG. 1 shows a schematic diagram of an exemplary embodiment of an electrochemical sensor arrangement 10 as well as of a breath alcohol measuring device 100 with such an electrochemical sensor arrangement 10. As was already mentioned above, the same principle was applicable to electrochemical sensor arrangements for gas sensors as well. Correspondingly, FIG. 1 further shows a gas sensor 100 with such an electrochemical sensor arrangement 10. The electrochemical sensor arrangement comprises an electrochemical sensor with at least two electrodes 12; 14. The electrochemical sensor further comprises, as is shown in FIG. 1, an electrolyte, which is provided in a membrane 13, which is arranged between the first electrode 12 and the second electrode 14 in the exemplary embodiment of FIG. 1. In this case, the electrochemical sensor may be, for example, an electrochemical fuel cell, which is suitable for carrying out a measurement of ethyl alcohol in human breath. As an alternative, the electrochemical sensor may be an electrochemical sensor for the detection of gas. For this, the electrochemical sensor arrangement may further comprise a third electrode, for example, a reference electrode. The electrochemical sensor arrangement 10 further comprises a heat source 16. This heat source is arranged such that it, on activation, selectively accurately heats one of the electrodes of the electrochemical sensor. Optionally, the electrochemical sensor arrangement further comprises a control device 20, as well as an output device 18. The control device can be configured here to carry out measurements by means of the electrochemical sensor. To this end, the electrochemical sensor arrangement further optionally comprises a measuring resistor 15, which is arranged between the terminals of the two electrodes. The output device can be activated by the control device to output measurement results and other information. Furthermore, the control device may be configured to control the heat source. The control device can therefore be coupled, for example, with the electrodes, with the heat source and with the optional output device.

The electrochemical sensor comprises the two electrodes 12; 14. These electrodes are called, for example, the measuring electrode and the counterelectrode in an electrochemical sensor. Based on a current flow between these two electrodes, a measurement is generally carried out by means of the electrochemical sensor. A potential is generated in the process between the electrodes during the measuring operation of the electrochemical sensor. An integral of the resulting current curve of the measured current between the electrodes is proportional here to the breath alcohol (to the ethyl alcohol in the breathing air) in case of use in a breath alcohol measuring device and can be used in a subsequent processing step to determine the breath alcohol. In this case, the integral of the current flow corresponds to the charge, which is an indicator of the alcohol concentration. For example, the measuring resistor 15 can be used for the measurement.

The electrochemical sensor arrangement further comprises a heat source 16, which is arranged such that it, upon activation, selectively heats one of the electrodes of the electrochemical sensor. In other words, the heat source is configured to selectively heat one of the two electrodes. "Selectively" here means that the heat source is arranged such that it heats one of the two electrodes much more than the other electrode, for example, so that at least twice as much heat energy is absorbed by the one electrode than by the other electrode and/or so that a temperature increase, for example, in degrees Celsius, resulting from the heating is at least twice as high in the one electrode than in the other electrode. In the ideal case, upon activation of the heat source, only the one electrode is heated; this will be the case only in a few embodiments because of a radiation of heat by the one electrode. In this connection, it is only relevant that one of the two electrodes is heated more than the other [electrode], so that an electric potential is generated between the electrodes. A voltage is thus generated between the electrodes due to the selective heating of the one electrode. In this case, both different types of heat sources and different embodiments of a heat transfer are taken into consideration.

For example, the heat source may be a light source, for example, an LED, or else even a halogen-based light source or a light bulb. Such an LED has a variety of advantages for the present application. On the one hand, it is thereby made possible that the one electrode is heated over a predefined time period, without the propagation of heat via a heat conductor having to be taken into consideration here, since the light penetrates the housing and is primarily adsorbed directly at the electrodes. The thermal disturbance (excitation) should be present only very briefly in order to be able to analyze the rapid dynamics. A thermal heating, which is based on the principle of heat conduction, is possibly less suitable, but also leads to the desired result. A bright LED has proven to be especially suitable as a radiation source, especially a blue LED. In the meanwhile, these LEDs are available for outputs up to 6 W and an efficiency of the radiation of above 70%. It was further determined in experiments that the energy of a UV LED is sufficient to generate a voltage, especially a photoelectric voltage. One advantage of an LED excitation is that the thermal energy can be brought to the sensor accurately and very briefly. The output can practically be switched on and switched off again without latency. In addition, the light source, for example, the LED, can be arranged entirely outside of the electrochemical sensor, as a result of which the concept may also be applied to conventional electrochemical sensors.

For example, the transfer of heat or the photoelectric influence of the electrode may be carried out in a wireless manner. Wireless is defined here by the influenced electrode not being wired with the heat source or with the light source. In other words, the transfer of heat and/or the transfer of light energy are carried out in a contactless manner or, generally speaking, the transfer of energy is carried out in a wireless manner and in a contactless manner. In this connection, for example, an LED, a thermal radiator, a light bulb or induction can be used. The light source, for example, the LED, may be arranged in this case such that the light emitted upon activation of the light source is absorbed by the one electrode, but not by the other electrode. In other words, the light source may be oriented such that the light emitted upon activation of the light source is directed towards the one electrode. The other electrode may be shadowed from the emitted light of the light source, for example, by the one electrode. To this end, the one electrode 12 may be arranged, for example, between the light source 16 and the other electrode 14.

As an alternative to light sources, other types of heat sources, for example, resistance heaters, may also be used. The heat may in these cases be transferred to the one electrode by means of a heat conductor. In other words, a heat source can be used in combination with a heat conductor to heat one of the electrodes accurately.

In some exemplary embodiments, the electrochemical sensor arrangement, as was already mentioned, comprises a control device 20. The control device may generally be configured to carry out measurements by means of the electrochemical sensor. The control device can be further configured to determine the vitality of the electrodes based on the selective heating of the one electrode. To this end, the control device can, on the one hand, be configured to activate the heat source in order to generate the voltage between the electrodes. On the other hand, the control device can be configured to measure the current flow based on the generated voltage and to determine the vitality of the electrochemical sensor based thereon. As a result, the control device can be configured to determine the vitality of the electrodes without using a test gas. The control device may, for example, be configured to carry out the process from FIG. 2a. More details for determining the vitality are therefore carried out in connection with the process from FIG. 2a.

The control device 20, as was stated above, may generally also be used to carry out measurements by means of the electrochemical sensor. The control device 20 may be configured in a measuring operation to set a potential between the electrodes of the sensor. In an electrochemical fuel cell, a potential of a measuring electrode is to be seen in relation to the reference electrode, i.e., the potential is a potential difference between the potential of the reference electrode and the potential of the measuring electrode. Hence, one of the electrodes of the electrochemical sensor may be the measuring electrode, and the other electrode may be the reference electrode. The potential at the measuring electrode can be set, for example, via a so-called potentiostatic control circuit, a circuit, in which a current flow is generated between the measuring electrode and the counterelectrode. The control device may comprise, for example, a potentiostatic control circuit or a different control circuit, which is suitable for setting the potential. As an alternative, the electrochemical sensor can be used as a pure fuel cell, and the current flow in the fuel cell can be determined. The control device can be further configured to carry out the measurement of a current between the measuring electrode and the counterelectrode during the measuring operation.

The electrochemical sensor arrangement, or the device which comprises the electrochemical sensor arrangement, for example, the breath alcohol measuring device comprises a graphic output unit in at least some exemplary embodiments. In this case, a plurality of types of graphic output units are conceivable. For example, the graphic output unit may be a display screen, for example, a liquid-crystal display screen, or a display screen, which is based on an organic light-emitting diode (OLED) technology. As an alternative, the graphic output unit may be based on a seven-segment display or on one or more status LEDs. The graphic output unit may be used to output information on the vitality of the sensor. For example, the control device may be configured to output the information on the vitality of the sensor via the graphic output unit. In this case, the information on the vitality of the electrodes is determined based on the selective heating of the one electrode. Further details to this end are proposed in connection with the process from FIG. 2a.

The control device 20 may correspond to any desired controller or processor or to a programmable hardware component in exemplary embodiments. For example, the control device 20 may also be embodied as software, which is programmed for a corresponding hardware component. To this extent, the control device 20 can be embodied as programmable hardware with correspondingly adapted software. Any desired processors such as digital signal processors (DSPs) may be used here. Exemplary embodiments are not limited here to a defined type of processor. Any desired processors or even a plurality of processors are conceivable for the embodiment of the control device 20.

More details and aspects of the electrochemical sensor arrangement or of the breath alcohol measuring device are mentioned in conjunction with the concept or examples, which are described before or afterwards, e.g., in FIG. 2. The electrochemical sensor arrangement or the breath alcohol measuring device may comprise one or more additional optional features, which correspond to one or more aspects of the proposed concept or of the described examples, as they were described before or afterwards.

Figure 2A:
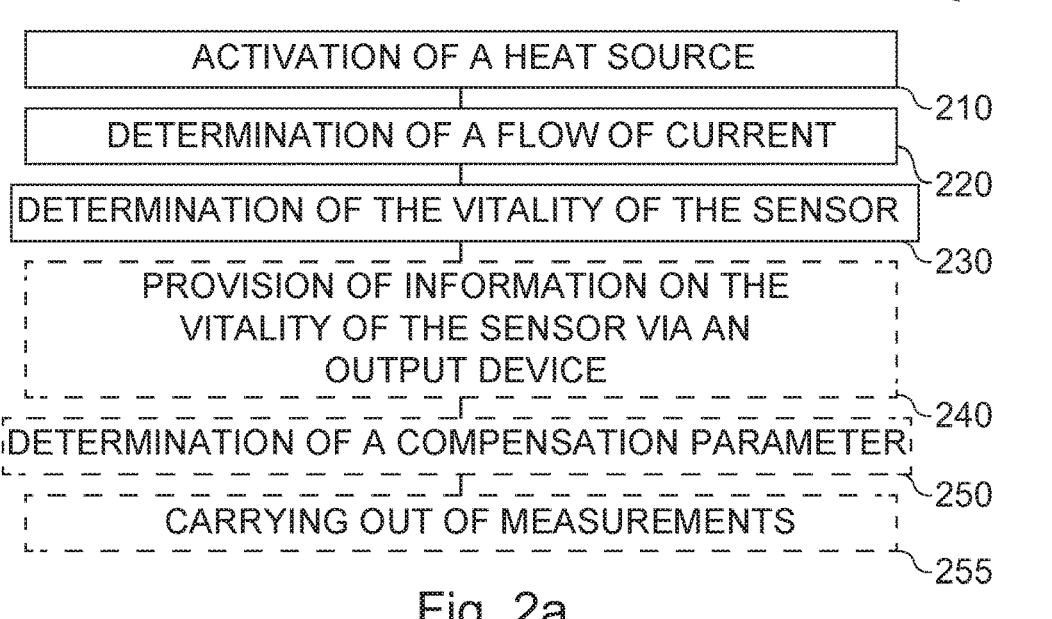
FIG. 2a is a flow chart of an exemplary embodiment of a process for determining a vitality of electrodes of an electrochemical sensor.

FIG. 2a shows a flow chart of an exemplary embodiment of a process 200 for determining a vitality of electrodes of an electrochemical sensor, for example, of the electrochemical sensor from FIG. 1. The process comprises an activation 210 of a heat source, for example, the heat source 16 from FIG. 1, or of a radiation source over a predefined time period in order to selectively heat one of the electrodes of the sensor, for example, the electrode 12 of the electrochemical sensor from FIG. 1. The process further comprises a determination 220 of a current flow between the electrodes of the electrochemical sensor. The current flow is based on a voltage, which is caused by the one selective heating of the one electrode by the heat source or by a selective irradiation of the one electrode by a UV source. Furthermore, the process comprises a determination 230 of the vitality of the sensor based on a signal shape of the current flow.

FIG. 2b shows a schematic block diagram of an exemplary embodiment of a corresponding control device 20 for determining the vitality of the electrodes of the electrochemical sensor. In this case, the control device 20 may correspond to the control device 20, as it was proposed in connection with FIG. 1. The control device may comprise, for example, an interface 22 and one or more processors 24, which are coupled with the interface. In this connection, the functionality of the control device may be provided by the one or more processors, wherein the detection and output of signals, for example, for and/or from the electrodes, the heat source or the output device, is carried out via the interface. The control device 20 is configured to carry out the process from FIG. 2. To this extent, the functionality of the control device is explained below with reference to the process as well. The process can generally by carried out, for example, by a device, which comprises the electrochemical sensor and the heat source, for example, by the control device of the device. In this case, the device may be, for example, a breath alcohol measuring device.

The process comprises the activation 210 of the heat source over a predefined time period in order to selectively heat one of the electrodes of the sensor. The activation of the heat source may comprise, for example, a provision of a control signal for the heat source, or for a power supply of the heat source, in order to activate the heat source. As an alternative, the activation of the heat source may comprise a provision of a power supply for the heat source, for example, when the heat source can be directly supplied with sufficient power by the control device. This may be, for example, the case when the heat source is an LED that can be operated with a few watts of power. In some exemplary embodiments, the thermal effect can be used to generate a voltage between the electrodes. In addition or as an alternative, the photoelectric effect can be used. The heat source can therefore be controlled such that one of the electrodes is thermally or even photoelectrically excited by the heat source, for example, by emitting light onto the one electrode over a predefined time period to generate the voltage between the electrodes.

The process further comprises the determination 220 of the flow of current between the electrodes of the electrochemical sensor. In this connection, the flow of current, as was already mentioned in connection with FIG. 1, is based on the voltage, which is caused by the one selective heating of the one electrode by the heat source. The determination of the flow of current can be carried out in this case in a manner similar to the measurement of the current between the measuring electrode and the counterelectrode during the measuring operation of an electrochemical sensor arrangement which comprises the electrochemical sensor. The measured current can in the process be recorded over a plurality of sampling points (samples) and can be provided in a storage device, for example, of the control device, for a subsequent analysis.

Furthermore, the process comprises the determination 230 of the vitality of the sensor based on the signal shape of the current flow. The signal shape of the current flow can be determined here, for example, on the plurality of recorded sampling points. As a result, the determination of the vitality of the sensor may comprise a determination of the signal shape based on the plurality of recorded sampling points of the measured current. If the signal shape is available, then one or more parameters of the signal shape can be analyzed to determine the vitality of the electrochemical sensor.

One parameter pertains to the duration that is needed to reduce the generated voltage again. As a result, the vitality of the sensor can be determined based on a time period between a first time, at which the voltage was generated, and a second time, at which the current flow has fallen below a threshold value after the generation of the voltage. In this case, the time period may be indicative of the vitality of the electrodes. The shorter the time period is, the "faster" is the electrochemical sensor, and the higher is the vitality of the sensor.

In addition or as an alternative, it is possible to use the shape of a signal peak of the signal shape to determine the vitality of the sensor. For example, the vitality of the sensor can be determined based on a height or slope of the signal peak in the signal shape. The higher the signal peak is, or the more steep the signal peak is, the higher is the vitality of the sensor. As an alternative or in addition, a component of the signal shape, which follows the signal peak, can be taken into consideration. Electrochemical sensors with a high vitality can, for example, be detected by the signal peak following an undershooter, which cannot be seen in case of dried-out electrochemical sensors. As a result, the vitality of the electrodes can be determined based on an undershooting in the signal shape after a signal peak in the signal shape.

In various exemplary embodiments, the process further comprises a provision 240 of information on the vitality of the sensor via a graphic output unit. In this connection, various embodiments of the graphic output unit were already proposed in connection with FIG. 1. The graphic output unit may especially be a display screen, a seven-segment display, or a graphic output unit that is based on one or more LEDs. The information on the vitality of the sensor may in this connection represent the vitality of the sensor. In a first embodiment, the information on the vitality of the sensor may indicate whether the electrochemical sensor is sufficiently vital (and thus also sufficiently accurate or rapid enough to be used in the field operation). The information on the vitality of the sensor may in this case be displayed, for example, via a single LED (wherein, for example, a green lighting of the LED means that the electrochemical sensor is sufficiently vital, and a red lighting of the LED means that the electrochemical sensor is no longer sufficiently vital). In another embodiment, more than two states can be distinguished. Thus, for example, the information on the vitality can display one of three states, good, average or poor, or "satisfactory," "still sufficiently vital (but no longer satisfactory)," and "no longer sufficiently vital." In this case, the corresponding information on the vitality may also be outputted via an LED (for example, "green," "yellow," "red"), or via a display screen of the device. The vitality of the sensor may also be outputted via a display screen of the device in a percentage display or a bar graph. For example, the output can be provided if the vitality of the electrodes violates a threshold value, for example, if the state is "still sufficiently vital" or "no longer sufficiently vital," or if a calculated percentage violates the threshold value. In other cases, the output may be omitted. In various embodiments, the vitality can be detected in the field, wherein a timely warning of the customer in case of a weak sensor can be outputted in the sense of a preventive maintenance. For example, a routine vitality check can be carried out, e.g., when the device is started.

In some exemplary embodiments, the information on the vitality may also comprise information on a prediction of a course of the vitality, apart from the information on the current vitality of the sensor. Such a prediction may be useful since the vitality of the sensor has an effect on the accuracy of the sensor; if only the vitality of the sensor changes, then the estimated accuracy also changes. Based on the projection, it is possible to determine for how long the sensor will still be sufficiently accurate, taking a predefined minimal measuring accuracy into consideration. For example, the signal shape can be used to determine not only the current vitality of the sensor, but also to determine for how long the sensor will be sufficiently vital. To this end, the determination 230 of the vitality of the sensor may comprise a projection of the vitality of the sensor, for example, based on a change in the signal shape, and of the correspondingly determined vitality of the sensor, over a plurality of measurements, wherein the plurality of measurements have taken place, for example, over several days, weeks or months. For example, the projection of the vitality of the sensor may comprise the carrying out of a time series projection based on the change in the vitality of the sensor over a plurality of measurements. For example, a fitting algorithm may be used for this purpose. Based on the projection, it is possible to determine for how long the sensor will still likely be usable, taking a predefined minimal measuring accuracy into consideration. For example, a look-up table can be used to infer a projection of the estimated accuracy of the electrochemical sensor from the projection of the vitality of the sensor. This estimation can subsequently be compared with a predefined minimal measuring accuracy. As a result, the information on the vitality of the sensor may comprise information on an estimated remaining duration of a usability of the electrochemical sensor, taking a predefined minimal measuring accuracy into consideration. In this case, the information on the estimated remaining duration of the usability may have, for example, a granularity of months; in addition, the estimation may be configured as conversative. For example, the information on the estimated remaining duration may display the usability, that the electrochemical sensor can still be used for at least a displayed number of months before the electrochemical sensor has to undergo maintenance or be replaced. Here, likewise the output can be provided if the estimated remaining duration is below a threshold value.

In some exemplary embodiments, the determined vitality of the sensor may also be used to adapt the results of the measurements that are carried out by means of the sensor and thus to increase the accuracy. As already mentioned above, the accuracy of the sensor is dependent on the vitality of the sensor. In this connection, there is in many cases a dependence between the vitality of the sensor and a deviation of the measurement result. This deviation may be, for example, related to the configuration; if the vitality of the sensor is known, a compensation parameter can then be calculated from this in order to compensate this deviation. As a result, the process may comprise a determination 250 of a compensation parameter based on the vitality of the sensor. The compensation parameter may depict to what extent the vitality of the sensor has an effect on the measurements of the sensor. Adaptation of the compensation parameter can thus be carried out for the purpose of improving the accuracy. As a result, longer adjustment intervals can be achieved due to the improved accuracy. For example, the compensation parameter may depict the above-mentioned deviation. Then, the compensation parameter can be calculated, for example, based on the determined vitality, for example, based on a mathematical function or based on another look-up table. The process may further comprise a carrying out 255 of measurements by means of the electrochemical sensor, taking the compensation parameter into consideration. The measurement results of the measurement can be based on the compensation parameter. Due to the use of the proposed concept, the vitality parameters can be determined in the field and the compensation parameters, which are needed for the analysis of the measurement result of an alcohol measurement, can be adapted. As a result, the accuracy of the measurement increases. In addition, this improved accuracy may be used to calculate the estimated remaining duration of the usability of the electrochemical sensor. Thus, an adjustment interval may also be extended. In some embodiments, a determination of the accuracy may also be carried out in the field without alcohol, or the adjustment may be carried out subsequently in the field, for example, based on the compensation parameter.

The determination of the vitality can be triggered by different events. The determination of the vitality can, for example, be carried out at regular times, for example, when the device is started. In this connection, the determination of the vitality may be, for example, a part of the self-test of the device. In other words, the process may be carried out by a device, which comprises the electrochemical sensor and the heat source and correspondingly the control device. The process, for example, the determination of the vitality of the sensor, may be carried out as part of a self-test of the device. The self-test of the device may be carried out, for example, when the device is started, or at the request of a user of the device.

The determination of the vitality can be further used to determine whether the sensor is connected according to specifications and in good working order in some exemplary embodiments. This may happen, for example, with a function test, in which it is checked whether a potential can be established between the electrodes, and whether a current flow between the electrodes can be measured. In addition, a physical sensor detection, e.g., due to the analysis of the sensor response by a voltage pulse, may also be replaced with the proposed concept. The present invention is not limited here only to alcohol sensors, but it may also be applied to other electrochemical sensors. The process may comprise a carrying out of a function test of the electrochemical sensor, wherein the function test is based on the determination of the vitality of the electrodes. If it is determined during the determination of the vitality of the electrodes that a current flow is measured between the electrodes, then the function test can be considered to be passed.

The interface 22 may correspond, for example, to one or more inputs and/or one or more outputs for receiving and/or transmitting information, for example, in digital bit values, based on a code, within a module, between modules, or between modules of different entities.

In exemplary embodiments the one or more processors 24 can correspond to any desired controller or processor or to a programmable hardware component. For example, the functionality of the one or more processors 24 may also be embodied as software that is programmed for a corresponding hardware component. In this connection, any desired processors, such as digital signal processors (DSPs) can be used. Exemplary embodiments are not limited here to a certain type of processor.

More details and aspects of the process and of the control device are mentioned in conjunction with the concept or examples, which were described before, e.g., in FIG. 1. The process and the control device may comprise one or more additional optional features, which correspond to one or more aspects of the proposed concept or of the described examples, as they were described before or afterwards.

Laboratory measurements were carried out to prove the method. To this end, a device was built in order to record the raw values of the electrochemical sensor and to activate a blue LED. The LED was placed above the electrochemical sensor and was operated, current regulated, for precisely 1,000 msec with reduced power, e.g., 500 mA. As a result of the thermoelectric voltage, this irradiation leads to a change in the measured value of the electrochemical sensor.

In a first test, a healthy sensor was measured. FIG. 3a shows measured values 300 of a healthy electrochemical sensor in an exemplary test setup. The sensor responds clearly to the irradiation. After less than a second, the decaying edge has already passed through the zero line. In addition, a characteristic undershooting can be detected.

For another test, an electrochemical sensors was dried artificially. The measured values 310 of a healthy (vital) electrochemical sensor and the measured values 320 of a dried-out electrochemical sensor were subsequently generated. FIG. 3b shows the measured values of the two sensors.

The dry sensor shows a markedly changed behavior. The signal peak of the current is reduced. The decaying edge has become markedly slower. An undershooter can no longer be detected. A slow sensor can be detected on the basis of this changed dynamics.

Figure 3C:
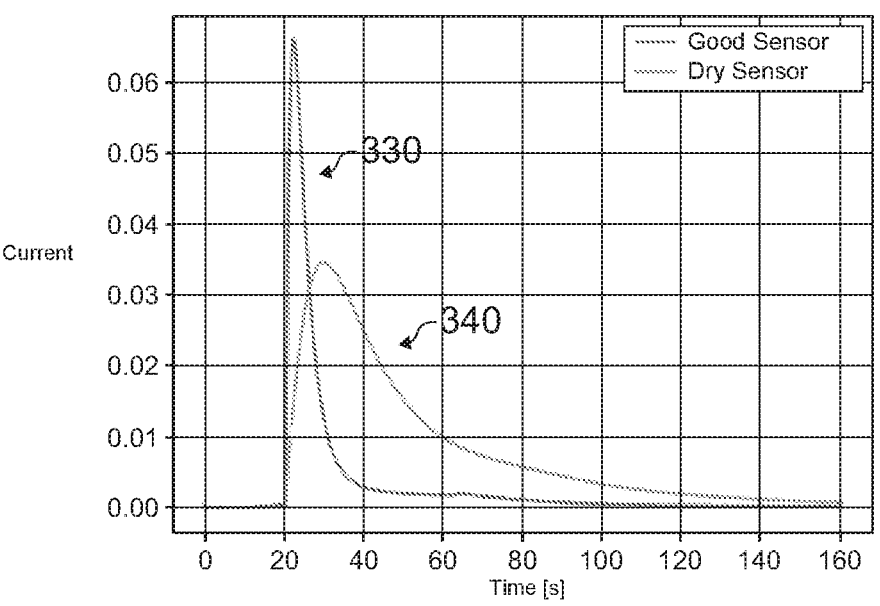
FIG. 3c is a graph showing ethyl alcohol time course from a healthy and from a dried-out electrochemical sensor in another exemplary test setup.

After the tests, the sensors were once again gassed with dry gas with ca. 380 ?g/L ethyl alcohol. FIG. 3c shows a comparison of the ethyl alcohol curve 330 of the vital sensor and of the ethyl alcohol curve 340 of the dry sensor. The dry sensor has become markedly slow due to the drying out, but is nevertheless still measurable.

Figure 4:
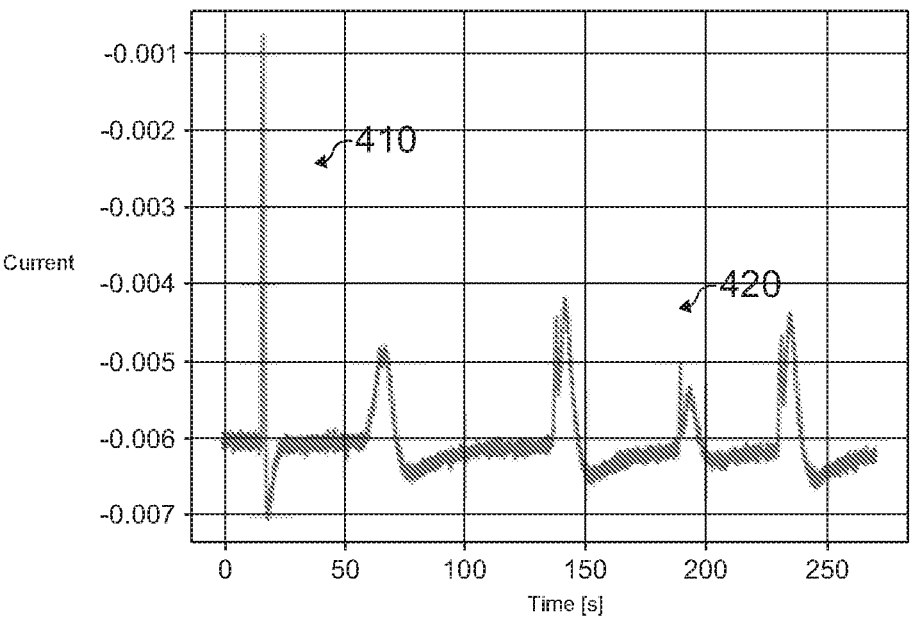
FIG. 4 is a graph showing measurement results of a test setup, in which an electrode of an electrochemical sensor was alternatively heated in a contactless manner by an LED and by a soldering iron.

In another test, a soldering iron was used as the heat source. Because of its high temperature, e.g., 400° C., the soldering iron emits a considerable part of its energy as heat radiation. Instead of LED, the soldering iron was held in a contactless manner briefly over the electrochemical sensor. The LED peak (summit) differs from the soldering iron peak in this case. The soldering iron peak consists of two superimposed peaks. These were less high than the LED peak in the test setup; in addition, the LED peak decayed more rapidly than the soldering iron peaks. FIG. 4 shows the measurement results of the test setup. In this case, peak 410 is the LED peak, and the subsequent peaks 420 are peaks, which were caused by the soldering iron. The reason for the signal shape is probably that the first fast peak is a result of IR radiation, which penetrates the sensor and leads to an increase in temperature on the electrode surface. The second peak is probably a result of the warming up of the sensor housing and of the subsequent slow heat conduction. This effect is still effective even if the soldering iron was again already removed a long time ago. By contrast, the greatest part of the LED radiation penetrates the sensor and reacts directly on the electrode surface, i.e., in the sensor interior. In this case, a thermoelectric voltage is induced due to the increase in temperature. Slow heat condition effects do not occur. This shows the advantages in case of using an LED as a radiation source.

In another test, the housing of an electrochemical sensor was made essentially impermeable to light and then irradiated with an LED. In a repetition of the test, only a fraction of the LED light could penetrate the sensor; instead of this, the housing was heated. In this connection, only an insignificant difference between the heating via a soldering iron and the heating via the LED was detectable in the corresponding measurements. In this case, the peak height of the LED peak was markedly reduced, and the overall duration was increased.

More details and aspects of the concept are mentioned in conjunction with the concept or examples, which were described before, e.g., in FIGS. 1 through 2b. Exemplary embodiments of the concept may comprise one or more additional optional features, which correspond to one or more aspects of the proposed concept or of the described examples, as they were described before or afterwards.

The aspects and features, which are described together with one or more of the examples and figures detailed before, may also be combined with one or more of the other examples, in order to replace an identical feature of the other example or to additionally introduce the feature into the other example.

Examples may, furthermore, be a computer program with a program code for carrying out one or more of the above processes or may pertain thereto when the computer program is executed on a computer or processor. Steps, operations or processes of different processes described above may be carried out by programmed computers or processors. Examples may also cover program storage devices, e.g., digital memory media, which are machine-readable, processor-readable or computer-readable and code machine-executable, processor-executable or computer-executable programs of instructions. The instructions carry out some of the steps or all the steps of the above-described processes or cause them to be carried out. The program storage devices may comprise or be, e.g., digital storage media, magnetic storage media, for example, magnetic disks and magnetic tapes, hard disk drives or optically readable digital memory media. Other examples may also cover computers, processors or control units, which are programmed for carrying out the steps of the above-described processes, or (field) programmable logic arrays ((F)PLAs=(Field) Programmable Logic Arrays) or (field) programmable gate arrays ((F) PGA=(Field) Programmable Gate Arrays), which are programmed for carrying out the steps of the above-described processes.

Functions of different elements shown in the figures, including any function blocks designated as "means," "means for providing a signal," "means for generating a signal," etc. may be embodied in the form of dedicated hardware, e.g., "of a signal provider," "of a signal processing unit," "of a processor," "of a control unit," etc. as well as hardware able to execute software in conjunction with corresponding software. In case of provision by a processor, the functions may be provided by a single dedicated processor, by a single shared processor or by a plurality of individual processors, some of which or all of which can be shared. However, the term "processor" or "control unit" is by far not limited to hardware only able to execute software, but rather may comprise digital signal processor hardware (DSP hardware; DSP=Digital Signal Processor), network processor, application-specific integrated circuit (ASIC=Application Specific Integrated Circuit), field-programmable logic array (FPGA=Field Programmable Gate Array), read only memory (ROM=Read Only Memory) for storing software, random access memory (RAM=Random Access Memory) and nonvolatile storage device (storage). Other hardware, conventional and/or client-specific, may also be included.

A block diagram may represent, for example, a rough circuit diagram, which implements the principles of the disclosure. In a similar manner, a flow chart, a process chart, a state transition diagram, a pseudocode and the like may represent different processes, operations or steps, which are displayed, for example, essentially in a computer-readable medium and thus can be carried out by a computer or processor, regardless of whether such a computer or processor is explicitly shown. The processes disclosed in the description or in the patent claims may be implemented by a structural element, which has a medium for carrying out each of the respective steps of these processes.

It is obvious that the disclosure of a plurality of steps, processes, operations or functions disclosed in the description or in the claims shall not be interpreted as located in the defined order, if this is not explicitly or implicitly indicated otherwise, e.g., for technical reasons. Hence, these are not limited to a defined order by the disclosure of a plurality of steps or functions, unless these steps or functions are not interchangeable for technical reasons. Further, a single step, function, process or operation in some examples may include a plurality of partial steps, partial functions, partial processes or partial operations and/or be broken up into same. Such partial steps may be included and be part of the disclosure of the single step, if they are explicitly ruled out.

Furthermore, the following claims are herewith incorporated into the detailed description, where each claim may stand alone as a separate example. While each claim may stand alone as a separate example, it should be noted that, even though a dependent claim may refer in the claims to a defined combination with one or more other claims, other examples may also comprise a combination of the dependent claim with the subject or any other dependent or independent claim. Such combinations are explicitly proposed here, if it is not indicated that a defined combination is not intended. Further, features of one claim shall be included for each other independent claim, even if this claim is not made directly dependent on the independent claim.

While specific embodiments of the invention have been shown and described in detail to illustrate the application of the principles of the invention, it will be understood that the invention may be embodied otherwise without departing from such principles.

The invention claimed is:

1. An electrochemical sensor arrangement for a breath alcohol measuring device, the electrochemical sensor arrangement comprising:

an electrochemical sensor with at least two electrodes;

a heat source configured and arranged to, upon activation, controllably heat one of the electrodes of the electrochemical sensor more than another; and a control device configured to determine a vitality of the electrodes based on the controlled heating of the one electrode and based on a voltage between the electrodes generated by the controlled heating and a current flow generated thereby.

2. An electrochemical sensor arrangement in accordance with claim 1, wherein the heat source is a light-emitting diode, LED.

3. An electrochemical sensor arrangement in accordance with claim 2, wherein the control device is configured to:

activate the heat source over a predefined time period in order to controllably heat the one electrode of the sensor;

determine a flow of current between the electrodes of the electrochemical sensor, wherein the flow of current is based on a voltage, which is caused by the one controlled heating of the one electrode by the heat source; and determine a vitality of the sensor based on a signal shape of the flow of current.

4. An electrochemical sensor arrangement in accordance with claim 3, further comprising a graphic output unit configured to output information on a vitality of the sensor, wherein information on a vitality of the electrodes is determined based on the controlled heating of the one electrode.

5. An electrochemical sensor arrangement in accordance with claim 1, wherein the control device is configured to:

activate the heat source over a predefined time period in order to controllably heat the one electrode of the sensor;

determine a flow of current between the electrodes of the electrochemical sensor, wherein the flow of current is based on a voltage, which is caused by the one controlled heating of the one electrode by the heat source; and determine a vitality of the sensor based on a signal shape of the flow of current.

6. An electrochemical sensor arrangement in accordance with claim 1, further comprising a graphic output unit configured to output information on a vitality of the sensor, wherein information on a vitality of the electrodes is determined based on the controlled heating of the one electrode.

7. A process for determining a vitality of electrodes of an electrochemical sensor of an electrochemical sensor arrangement, the process comprising:

activating a heat source over a predefined time period to controllably heat one of the electrodes of the electrochemical sensor more than another of the electrodes of the electrochemical sensor;

determining a flow of current between the electrodes of the electrochemical sensor, wherein the flow of current is based on a voltage, which is caused by the one controlled heating of the one electrode by the heat source; and determining the vitality of the sensor based on a signal shape of the flow of current.

8. A process in accordance with claim 7, further comprising providing information on the vitality of the sensor via a graphic output unit.

9. A process in accordance with claim 8, wherein the information on the vitality of the sensor comprises information on an estimated remaining duration of a usability of the electrochemical sensor, based on a predefined minimal measuring accuracy.

10. A process in accordance with claim 7, wherein the process is carried out by the electrochemical sensor arrangement, comprising a device that comprises the electrochemical sensor and the heat source, wherein the process is carried out as part of a self-test of the device.

11. A process in accordance with claim 7, further comprising:

determining a compensation parameter based on the vitality of the sensor, the compensation parameter depicting to what extent the vitality of the sensor has an effect on the measurements of the sensor; and carrying out measurements by means of the electrochemical sensor based on the compensation parameter.

12. A process in accordance with claim 7, wherein the electrochemical sensor arrangement comprises a control device configured to determine the vitality of the electrodes based on the controlled heating of the one electrode and based on a voltage between the electrodes generated by the controlled heating and a current flow generated thereby.

13. A process in accordance with claim 12, wherein a graphic output unit is provided that is configured to output information on a vitality of the sensor, wherein information on a vitality of the electrodes is determined based on the controlled heating of the one electrode.

14. A process in accordance with claim 12, wherein the heat source comprises a light-emitting diode.

15. A breath alcohol measuring device comprising an electrochemical sensor arrangement, the electrochemical sensor arrangement comprising:

an electrochemical sensor with at least two electrodes;

a heat source configured and arranged to, upon activation, controllably heat one of the electrodes of the electrochemical sensor more than another of the electrodes of the electrochemical sensor; and a control device configured to determine a vitality of the electrodes based on the controlled heating of the one electrode and based on a voltage between the electrodes generated by the controlled heating and a current flow generated thereby.

16. A breath alcohol measuring device in accordance with claim 15, wherein the heat source comprises a light-emitting diode.

17. A breath alcohol measuring device in accordance with claim 16, wherein the control device is configured to:

activate the heat source over a predefined time period in order to controllably heat the one electrode of the sensor;

determine a flow of current between the electrodes of the electrochemical sensor, wherein the flow of current is based on a voltage, which is caused by the one controlled heating of the one electrode by the heat source; and determine a vitality of the sensor based on a signal shape of the flow of current.

18. A breath alcohol measuring device in accordance with claim 16, further comprising a graphic output unit configured to output information on a vitality of the sensor, wherein information on a vitality of the electrodes is determined based on the controlled heating of the one electrode.

19. A breath alcohol measuring device in accordance with claim 16, wherein the light-emitting diode is arranged entirely outside of the electrochemical sensor.

20. A breath alcohol measuring device in accordance with claim 15, wherein the control device is configured to:

activate the heat source over a predefined time period in order to controllably heat of the one electrode of the sensor;

determine a flow of current between the electrodes of the electrochemical sensor, wherein the flow of current is based on a voltage, which is caused by the one controlled heating of the one electrode by the heat source; and determine a vitality of the sensor based on a signal shape of the flow of current.

21. A breath alcohol measuring device in accordance with claim 15, further comprising a graphic output unit configured to output information on a vitality of the sensor, wherein information on a vitality of the electrodes is determined based on the controlled heating of the one electrode.

22. A breath alcohol measuring device in accordance with claim 15, wherein the heat source comprises a light source and the light source is positioned such that the one electrode is arranged between the light source and the other electrode.

* * * * *